United States Patent

Rowe

(10) Patent No.: US 6,616,650 B1
(45) Date of Patent: **\*Sep. 9, 2003**

(54) METHOD AND APPARATUS FOR DELIVERY OF THERAPEUTIC AGENT

(75) Inventor: Stanton J. Rowe, Miami Lakes, FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/609,633

(22) Filed: Jul. 3, 2000

Related U.S. Application Data

(62) Division of application No. 07/865,781, filed on Apr. 7, 1992, now Pat. No. 6,146,358, which is a continuation of application No. 07/322,929, filed on Mar. 14, 1989, now abandoned.

(51) Int. Cl.[7] .............................................. A61M 31/00
(52) U.S. Cl. .................. 604/509; 604/103.02; 604/523; 606/194; 623/1.11
(58) Field of Search ...................... 604/890.1, 507–510, 604/96.01, 101.04, 103.02, 103.01, 103.05–103.08, 103.11–103.14, 104, 265, 266, 523; 606/192, 194; 623/1.1, 1.11, 1.15, 1.41, 1.42–1.44, 1.46, 1.5, 1.51, 1.53

(56) References Cited

U.S. PATENT DOCUMENTS

| Patent No. | Date | Inventor | Ref. |
|---|---|---|---|
| 2,499,045 A | 2/1950 | Walker et al. | |
| 3,173,418 A | 3/1965 | Baran | |
| 3,334,629 A | 8/1967 | Cohn | |
| 3,610,247 A | 10/1971 | Jackson | |
| 4,029,104 A | 6/1977 | Kerber | |
| 4,213,461 A | 7/1980 | Pevsner | |
| 4,423,725 A | 1/1984 | Baran et al. | |
| 4,471,779 A | 9/1984 | Antoshkiw et al. | |
| 4,636,195 A | 1/1987 | Wolinsky | |
| 4,638,805 A | 1/1987 | Powell | |
| 4,693,243 A | 9/1987 | Buras | |
| 4,711,251 A | 12/1987 | Stokes | |
| 4,713,402 A | 12/1987 | Solomon | |
| 4,733,665 A | 3/1988 | Palmaz | |
| 4,738,666 A | 4/1988 | Fuoua | |
| 4,739,762 A | 4/1988 | Palmaz | |
| 4,740,207 A | 4/1988 | Kreamer | |
| 4,753,652 A | * 6/1988 | Langer et al. | 623/1 |
| 4,769,013 A | 9/1988 | Lorenz et al. | |
| 4,773,901 A | 9/1988 | Norton | |
| 4,821,722 A | 4/1989 | Miller et al. | |
| 4,877,030 A | * 10/1989 | Beck et al. | 128/343 |
| 4,900,303 A | 2/1990 | Lemelson | |
| 4,921,483 A | * 5/1990 | Wijay et al. | 604/96 |
| 4,922,905 A | * 5/1990 | Strecker | 606/195 |
| 4,923,450 A | 5/1990 | Maeda et al. | |
| 4,929,602 A | * 5/1990 | Harker et al. | 514/18 |
| 4,946,466 A | 8/1990 | Pinchuk et al. | 606/194 |
| 4,961,954 A | * 10/1990 | Goldberg et al. | 427/2 |
| 4,979,959 A | * 12/1990 | Guire | 623/66 |
| 5,019,090 A | * 5/1991 | Pinchuk | 606/194 |
| 5,019,393 A | * 5/1991 | Ito et al. | 424/423 |
| 5,049,131 A | 9/1991 | Deus | |
| 5,059,211 A | * 10/1991 | Stack et al. | 606/198 |
| 5,087,244 A | 2/1992 | Wolinsky et al. | |
| 5,102,402 A | 4/1992 | Dror et al. | |
| 5,102,417 A | * 4/1992 | Palmaz | 606/195 |
| 5,167,960 A | * 12/1992 | Ito et al. | 424/423 |
| 5,195,984 A | * 3/1993 | Schatz | 606/195 |
| 5,213,580 A | * 5/1993 | Slepian et al. | 128/898 |
| 5,893,840 A | 4/1999 | Hull et al. | |

* cited by examiner

*Primary Examiner*—Brian L. Casler
*Assistant Examiner*—Cris L. Rodriguez
(74) *Attorney, Agent, or Firm*—George H. Gerstman; Seyfarth Shaw

(57) ABSTRACT

A therapeutic agent is applied to an internal tissue site of a patient by advancing typically a catheter into the patient to cause a portion of the catheter, typically a catheter balloon, to occupy the internal site. The balloon portion of the catheter carries the therapeutic agent, usually mixed with a controlled release carrier for the agent, typically on an outer surface of the section, to permit release thereof from the catheter balloon at the internal tissue site so that the therapeutic agent is locally applied to the internal tissue site.

2 Claims, 1 Drawing Sheet

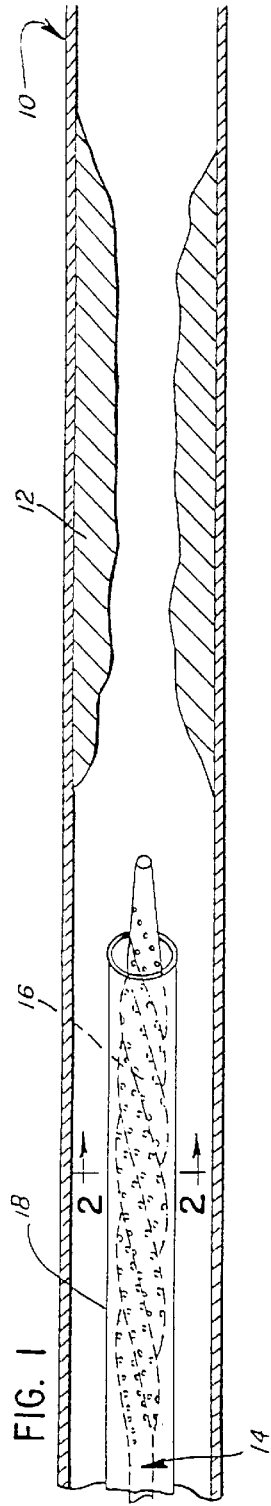
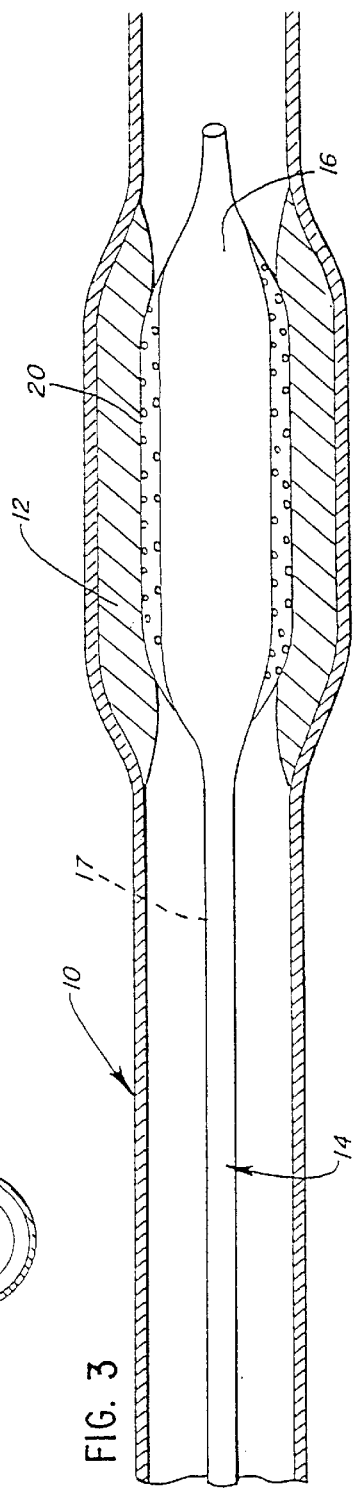
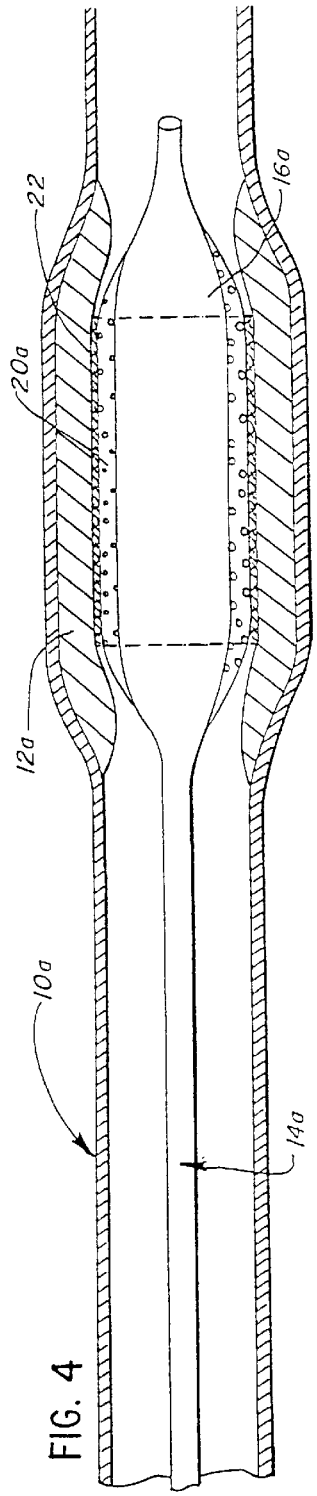

METHOD AND APPARATUS FOR DELIVERY OF THERAPEUTIC AGENT

This application is a division of U.S. application Ser. No. 07/865,781, filed Apr. 7, 1992, now U.S. Pat. No. 6,146,358 which is a continuation of U.S. application Ser. No 07/322,929, filed Mar. 14, 1989 now abandoned.

BACKGROUND OF THE INVENTION

The present invention relates to a method and apparatus for delivering a therapeutic agent to a localized internal tissue site within a patient. While various techniques are presently known in the prior art for such localized delivery of a therapeutic agent, a disadvantage in such techniques often exists in that the presence of the therapeutic agent is, often transient. The agent is typically washed away by moving fluids within the body, or quickly neutralized by biochemical processes.

Techniques are known to the art for the localized delivery of therapeutic agent by means of a small catheter which extends from the exterior of the patient to the internal tissue site, with a mechanical delivery system being provided to administer the therapeutic agent in a continuous, or periodic, controlled dosage over a substantial period of time. However, this requires the continuing presence of the catheter in the body, and the patient remains connected to the mechanical controlled delivery mechanism.

As another technique, controlled release members are surgically implanted into the patient, for example a plastic mass in which the therapeutic agent is impregnated. Such a controlled release member provides desired controlled release of a therapeutic agent, but the plastic carrier member remains as an implant after the therapeutic agent has been exhausted, unless it is removed, which may require surgery.

In accordance with this invention, a new method and apparatus for delivering therapeutic agent is provided, preferably for delivery in a controlled release manner over a substantial period of time at the internal tissue site. Thus, the internal tissue site can be bathed in the therapeutic agent for such a substantial period of time without the necessary presence of an indwelling catheter, and preferably without the presence of a residual implant which must be later removed.

The method of this invention may be performed in conjunction with other medical procedures. For example, it may be performed in conjunction with the well known PTCA procedure pertaining to the balloon dilation of coronary arteries to improve blood flow. It is the current custom in a PTCA procedure or related procedures to delivery by injection up to about 10,000 units of heparin as a bolus during or immediately after the procedure, with hourly or additional doses of heparin being administered up to 24 hours after the PTCA procedure.

However, it is known that such a systemic delivery of heparin has significant potential side effects that may contraindicate the PTCA procedure for certain patients i.e., those who are subject to internal bleeding such as ulcer patients, or patients with high blood pressure.

The purpose of providing a dosage of heparin to the patient immediately after PTCA or the like is to prevent the clotting of blood at the site where the artery was dilated by the balloon catheter in the procedure. By this invention, it become possible to administer overall a much lower effective dosage of heparin by administering it locally at the site of the arterial stenosis which was dilated by the balloon catheter. This is done by the application of heparin or other therapeutic agent directly to the stenosis site. Preferably, the therapeutic agent so applied can exhibit a controlled release characteristic for a long, effective life even after the PTCA catheter has been withdrawn.

Additionally, one in three patients conventionally have a restenosis within six months at the same arterial site, so that the coronary artery occludes once again, often putting the patient into worse condition than he was before the original PTCA procedure. In accordance with this invention it is possible during the original PTCA procedure to provide slow release therapeutic agents that reside in and adjacent the tissue of the stenosis to suppress not only thrombosis, but also subintimal fibromuscular hyperplasia, resulting in regrowth of the stenosis.

The invention of this application can be used in a wide variety of medical procedures above and beyond the dilation of stenosis in coronary arteries. One may provide therapeutic agents to a variety internal tissue sites where such is needed, preferably resulting in a persistent dosage of medication at the site. The medication and carrier, when used, is preferably removed by biochemical processes to leave no significant residue at the internal tissue site.

DESCRIPTION OF THE INVENTION

This invention relates to a method of applying a therapeutic agent to an internal tissue site of a patient, which comprises: advancing an elongated member such as a catheter internally into a patient to cause a portion of the elongated member to occupy the internal tissue site. A portion of the elongated member comprises a lateral wall section which carries the therapeutic agent in a manner permitting release thereof from the lateral wall section at the internal tissue site.

One then effects such release of the therapeutic agent at the internal tissue site. Such a step of effecting the release may make use of a catheter balloon as the portion of the elongated member that carries the therapeutic agent. Hence, by inflation of the balloon, the therapeutic agent is pressed into tissue of the internal tissue site, at least some of the agent being retained there as the catheter balloon is once again deflated.

Also, the therapeutic agent is preferably mixed with a controlled release carrier for the agent and positioned on an outer surface of the lateral wall section of the elongated member, which preferably is a catheter balloon is discussed above. Such controlled release carriers are preferably biodegradable over a relatively long period of time, so that as they are brought into contact with the tissues of the internal tissue site, preferably by balloon inflation, at least some of the therapeutic agent and carrier is retained there for a relatively slow, controlled diffusion of the therapeutic agent out of the carrier. Then, preferably, the biodegradable carrier is itself, in due time, removed by natural body processes.

Thus, it becomes possible to apply to an internal tissue site a persistent dosage of therapeutic agent which, with the carrier, provides a slow, controlled release over a predetermined time of the therapeutic agent to the nearby tissues. By this means, heparin, for example, can be provided in adequate dosage to a stenosis site after a PTCA procedure without the need to provide a full dosage of heparin to the entire body. Thus, patients who are subject to bade side effects of heparin are in less danger, while the desired effect of the heparin or other therapeutic agent on the stenosis site or other tissue is provided.

Examples of controlled release carriers which might be used include semisynthetic polyacryl starch microparticles (or other biodegradable microparticles containing the therapeutic agent), ethyl cellulose, poly L-lactic acid, heptakis (2,6-di-o-ethyl)-beta-cyclodextrin, polyalkylcyanoacrylate nanocapsules, polymethyl acrylate, monocarboxycellulose, alginic acid, hyaluronic acid, lipid bilayer beads (liposomes), polyvinylpyrollidone, polyvinylalcohol, hyaluronic acid, albumin, lipid carriers of continuous phase (nonmicroparticle type), and known agents for transdermal sustained release of therapeutic agents.

Appropriate carrier materials may be cross-linked to increase their persistence in the internal tissue site. The cross-link density may be adjusted to provide varying release rates of the therapeutic agent as may be desired.

Therapeutic agents may be applied in accordance with this invention by means of a catheter or other elongated member having the therapeutic agent carried on a lateral wall section thereof. Such agents may include any medication which would be desirably applied locally to a specific internal tissue site that can be reached by the catheter or other elongated member.

Specific examples of such therapeutic agents include anti-thrombogenic agents or other agents for suppressing stenosis or late restenosis such as heparin, streptokinase, urokinase, tissue plasminogen activator, anti-thromboxane $B^2$ agents, anti-B-thromboglobulin, prostaglandin E, aspirin, dipyridimol, anti-thromboxane $A_2$ agents, murine monoclonal antibody 7E3, triazolopyrimidine, ciprostene, hirudin, ticlopidine, nicorandil, and the like. Anti-Platelet derived growth factor may be used as a therapeutic agent to suppress subintimal fibromuscular hyperplasia at an arterial stenosis site, or any other inhibitor of cell growth at the stenosis site may be.,used.

The therapeutic agent also may comprise a vasodilator to counteract vasospasm, for example an anti-spasmodic agent such as papaverine. The therapeutic agent may be vasoactive agents generally such as calcium antagonists, or alpha and beta adrenergic agonists or antagonists. Additionally, the therapeutic agent may include a biological adhesive such as medical grade cyanoacrylate adhesive or fibrin glue, the latter being for example to adhere an occluding flap of tissue in a coronary artery to the wall, or for a similar purpose.

Also, a balloon catheter in which the balloon is expanded to apply a stent to the coronary artery or elsewhere may be provided with a coating of heparin or other antithrombogenic agent along the balloon, preferably in conjunction with a controlled release carrier for the agent. Thus, simultaneously with the application of the stent, the anti-throrbogenic agent is applied to the internal tissue site for preferably long term suppression of thrombogenic activity in the vicinity of the stent.

Additionally, the therapeutic agent in accordance with this invention may be an anti-neoplastic agent such as 5-fluorouracil or any known anti-neoplastic agent, preferably mixed with a controlled release carrier for the agent, for the application of a persistent, controlled release anti-neoplastic agent to a tumor site.

The therapeutic agent may be an antibiotic which may be applied by this invention, preferably in conjunction with a controlled release carrier for persistence, to an infected stent or any other source of localized infection within the body. Similarly, the therapeutic agent may comprise steroids for the purpose of suppressing inflammation or for other reasons in a localized tissue site.

The therapeutic agent may constitute any desired mixture of individual pharmaceuticals or the like, for the application of combinations of active agents.

The catheter or other elongated member may preferably be advanced into tissues of the patient toward the internal tissue site while the portion carrying the therapeutic agent is enclosed in a protective sheath, to prevent removal of substantial amounts of the therapeutic agent from the catheter before reaching the desired internal site. The, the protective sheath may be withdrawn, to expose the catheter portion which carries the therapeutic agent. Then the therapeutic agent is applied to the tissues, for example by expansion of a catheter balloon upon which the therapeutic agent resides, or by other processes such as spontaneous dispersion off the catheter into the tissues. If desired, the protective sheath may be a conventional introducer catheter, or it may be a split introducer sheath to facilitate removal of the sheath from the catheter after its withdrawal.

DESCRIPTION OF DRAWINGS

In the drawings,

FIG. 1 is a schematic, enlarged view of the distal end of a PTCA catheter, modified in accordance with this invention, in an initial step of performing a PTCA procedure to expand a stenosis in a coronary artery by inflation of a balloon section on the catheter;

FIG. 2 is a sectional view taken along line 2—2 of FIG. 1;

FIG. 3 is a similar enlarged, schematic view showing the catheter of FIG. 1 with the balloon in inflated condition for the purpose of expanding the coronary artery stenosis; and FIG. 4 is a schematic view, similar to FIG. 2, showing a modification in which a conventional stent is carried on the catheter balloon section, and is being expanded to provide internal support against the arterial wall at the stenosis area, including the invention of this application.

DESCRIPTION OF SPECIFIC EMBODIMENTS

Referring to FIGS. 1 and 2, an enlarged view of a coronary artery 10 is shown in which an area of stenosis 12 exists. In this embodiment, the process and catheter of this invention is incorporated into an otherwise-conventional PTCA procedure. PTCA catheter 14 is provided, being of conventional design for such a catheter except as otherwise described herein. PTCA catheter has a balloon section 16 which may be of generally conventional design, but which is specifically shown to be modified in accordance with the teachings of Montano U.S. patent application Ser. No. 302,302, filed Jan. 26, 1989 and entitled Balloon Catheter. Balloon section 16 may be inflated through inflation lumen 17 of the catheter.

Catheter 14 is shown to be enclosed within an introducer catheter 18 of generally conventional design as catheter 14 is advanced toward the stenosis 12. Then, as shown in FIG. 3, introducer catheter 18 is withdrawn, preferably immediately prior to inserting the balloon section 16 of catheter 14 into the stenosis 12.

In accordance with this invention, catheter balloon 16 is coated with a therapeutic agent 20, intimately mixed with a controlled release carrier for the agent. In this specific embodiment, the therapeutic agent may be heparin mixed into the controlled release carrier in a concentration of typically 75 to 750 heparin units per milligram of controlled release carrier present. The therapeutic agent may be coated on the catheter balloon 16 to provide a coating having a thickness of typically 0.5 to 1.5 mm., so that as balloon 16 is inflated in conventional manner for PTCA, the coating 20 of controlled release carrier plus heparin is forcefully driven against the stenosis tissue 12 at a substantial force corresponding to the inflation pressure within balloon 16 of, typically, 7 to 17 atmospheres, for example about 10 atmospheres. Under this pressure, the material of coating 20 is forced into the stenosis tissue 12 through cracks and the like that are formed during the inflation process, between individual tissue portions, and by diffusion, to provide a persistent presence of the controlled release carrier and heparin on and in the stenosis 12.

Thereafter, after withdrawal of catheter 14 at the termination of PTCA, the heparin present in the controlled release carrier retained in and on the stenosis is slowly released over a period of time, to provide its desired medical effect immediately in the stenosis area to suppress thrombogenic, while the overall heparin dosage with respect to the total body is very low so that undesired side effects of the heparin administration are suppressed.

Additionally, the controlled release carrier may include not only heparin or another anti-thrombogenic agent as a therapeutic agent, but it may also include an effective dose of anti-platelet derived growth factor. In this manner, the stimulus to regrowth provided by platelet derived growth fact from platelets which adhere to the stenosis may be suppressed over a substantial period of time.

The controlled release carrier used may be selected from controlled release carriers listed above, with the specific selection being dependent upon the controlled release characteristics of the desired therapeutic agent from such carrier, the release characteristics of the therapeutic agent and carrier mixture from the catheter, the migration of the agent had carrier into the stenosis, and other known pharmaceutical parameters.

Thus, by a modification of the PTCA procedure in accordance with this invention, the procedure can take place with less or no i.v. administration of heparin as is customary, which opens up the possibility that patients who need the procedure but are at risk to high doses of heparin may have it. Additionally, the modification of this invention can reduce the number of patients who encounter a reoccurrence of the stenosis due to acute thrombosis, or due to stimulated cell growth in the stenosis area over the few months subsequent to the PTCA procedure.

Catheter 14 may also be used for the application of therapeutic agents to other tissue sites than stenosis 12. For example, the balloon 16 of catheter 14 may be coated with a controlled release carrier which carries an anti-neoplastic agent in the case where the catheter can be inserted into a tumor, so that upon inflation of the balloon the controlled release carrier and anti-neoplastic agent are pressed into the tumor for temporary retention there.

Additionally, balloon 16 or catheter 14 may carry an anti-spasmodic agent, either alone or in conjunction with an anti-thrombogenic agent and an agent for suppressing the growth of stenosis cells, to provide local administration of medication for suppressing of an arterial spasm. Additionally, antibiotics or steroids may be locally applied to a tissue site in similar manner, or a glue such as fibrin glue may be applied to a tissue tear.

Turning to FIG. 4, a modification of the invention of this application is provided. In this embodiment, as shown, a balloon catheter 1 4a similar to catheter 14 has been applied to a stenosis area 12a of a coronary artery or other artery 10a. Any optional introducer catheter that facilitated the introduction thereof has been withdrawn.

Balloon 16a, of similar design to the previous embodiment, carries about its exterior not only a layer or controlled release carrier 20a with admixed therapeutic agent, but also a wire mesh stent 22 of the expansible type and typically of conventional design.

FIG. 4 shows stent 22 being expanded by the pressurized balloon 16a into its permanently outwardly expanded position, to keep stenosis 12 from later collapsing inwardly, so that lumen of the artery 10a remains open. Simultaneously with the expansion process for emplacement of the stent, the layer 20a of controlled release carrier and therapeutic agent is forced outwardly between the interstices of stent 22, to force the carrier and therapeutic agent into stenosis 12a in a manner similar to the previous embodiment.

Typically, the therapeutic agent may once again be heparin, or another anti-thrombogenic agent, to suppress thrombogenic activity around both the stenosis 12a and the stent 22. If desired, as before, other therapeutic agents may be added, for example the anti-platelet derived growth factor, such therapeutic agents being typically provided in dosages as previously described. Generally, a slightly increased amount of the controlled release carrier and therapeutic agent will be provided to catheter balloon 16a to account for the interstices provided by the presence of stent 22, if it is desired to force a similar amount of carrier and therapeutic agent into the stenosis as in the previous embodiment.

As a further modification, the coating 20a of carrier and therapeutic agent may also include an antibiotic to prevent infection. Alternatively, in the event of infection around a previously applied stent, catheter 14a with an antibiotic-coated balloon 16a may be provided to administer a persistent antibiotic plus option carrier to the infection site about the stent.

If desired, catheters or flexible probes which do not carry a balloon may carry on or in it at least a section thereof the therapeutic agent, preferably admixed With a controlled release carrier. In this circumstance, it is typical to rely on natural diffusion processes to cause transfer of the therapeutic agent to the desired internal tissue site.

Thus, a new technique and apparatus is provided for the application of a therapeutic agent in localized manner to an internal tissue site, without administration of larger doses of the therapeutic agent to the patent. This can avoid undesired side effects of such large doses, while providing the therapeutic agent to the site where it is needed.

The above has been offered for illustrative purposes only, and is not intended to limit the scope of the invention, which is as defined in the claims below.

What is claimed is:

1. A method for inhibiting restenosis in a balloon angioplasty procedure in a human body lumen, comprising the steps of:

providing a balloon angioplasty catheter having a dilatation balloon carrying, on the exterior of the balloon, a drug for suppressing the growth of cells which form a stenosis, for affecting the interior of a human body lumen to inhibiting restenosis when the catheter is positioned and inflated therewithin;

providing a mesh expandable stent defining openings carried on the exterior of said balloon, said stent being positioned on said balloon over said drug;

inserting said balloon angioplasty catheter into a lumen at a stenosis where treatment is desired;

expanding said balloon and stent against the walls of the lumen forcing the drug outwardly between said openings into the stenosis without requiring heating of the drug; and removing said balloon angioplasty catheter with the expanded stent being in place within the body lumen and with the drug being applied to the body lumen in order to inhibit restenosis.

2. A method for inhibiting restenosis in a balloon angioplasty procedure in a human body lumen, comprising the steps of:

providing a balloon angioplasty catheter having a dilatation balloon carrying a controlled release carrier on the exterior of said balloon, said controlled release carrier carrying a drug or combination of drugs for suppressing the growth of cells which form a stenosis for affecting the interior of a human body lumen to inhibit restenosis when the catheter is positioned and inflated therewithin;

providing a mesh expandable stent defining openings carried on the exterior of said balloon, said stent being positioned on said balloon over said controlled release carrier;

inserting said balloon angioplasty catheter into a lumen at a stenosis where treatment is desired;

expanding said balloon and stent against the walls of the lumen, forcing the drug or combination of drugs outwardly between said openings into a stenosis without requiring heating of the drug; and removing said balloon angioplasty catheter with the expanded stent being in place within the body lumen and with the drug or combination of drugs being applied to the body lumen in order to inhibiting restenosis.

* * * * *